United States Patent
Nakanishi et al.

(10) Patent No.: US 6,925,201 B2
(45) Date of Patent: Aug. 2, 2005

(54) INSPECTION APPARATUS AND METHOD FOR ELECTRODE PLATE-CONNECTED STRUCTURE FOR SECONDARY CELL

(75) Inventors: Toshiaki Nakanishi, Aichi (JP); Yugo Nakagawa, Aichi (JP)

(73) Assignees: Matsushita Electric Industrial Co., Ltd., Osaka (JP); Toyota Jidosha Kabushiki Kaisha, Aichi (JP)

( * ) Notice: Subject to any disclaimer, the term of this patent is extended or adjusted under 35 U.S.C. 154(b) by 612 days.

(21) Appl. No.: 10/017,254

(22) Filed: Dec. 14, 2001

(65) Prior Publication Data

US 2002/0076094 A1 Jun. 20, 2002

(30) Foreign Application Priority Data

Dec. 14, 2000 (JP) .......................................... 2000-381106

(51) Int. Cl.⁷ ................................................. G06K 9/00
(52) U.S. Cl. ........................................ 382/141; 348/86
(58) Field of Search ............................... 382/141, 152, 382/146, 150; 348/86; 356/237.1

(56) References Cited

U.S. PATENT DOCUMENTS 3,773,422 A * 11/1973 Stavis et al. ................. 356/630
6,249,598 B1 * 6/2001 Honda et al. ................ 382/150

FOREIGN PATENT DOCUMENTS

| JP | 08-287962 | | 11/1996 | |
| JP | 11073948 A | * | 3/1999 | ............ H01M/4/04 |
| JP | 2000-100465 | | 7/2000 | |

\* cited by examiner

*Primary Examiner*—Bhavesh M. Mehta
*Assistant Examiner*—John Strege
(74) *Attorney, Agent, or Firm*—Snell & Wilmer L.L.P.

(57) ABSTRACT

The present invention provides an inspection apparatus for an electrode plate-connected structure for a secondary cell for inspecting each bonding portion of an electrode plate-connected structure for a secondary cell including a plurality of electrode plates which are arranged in parallel to one another at prescribed intervals and are perpendicularly connected to a power collecting plate. The apparatus is characterized by including: a lighting section for irradiating light to each of the bonded portions of the plurality of electrode plates and the power collecting plate; a light receiving section for detecting a projected image of each of the bonded portions based on the light irradiated to the electrode plate-connected structure by the lighting section; and an evaluation section for evaluating a bonding state of each of the bonding portions based on the projected image of each of the bonded portions detected by the light receiving section.

14 Claims, 11 Drawing Sheets

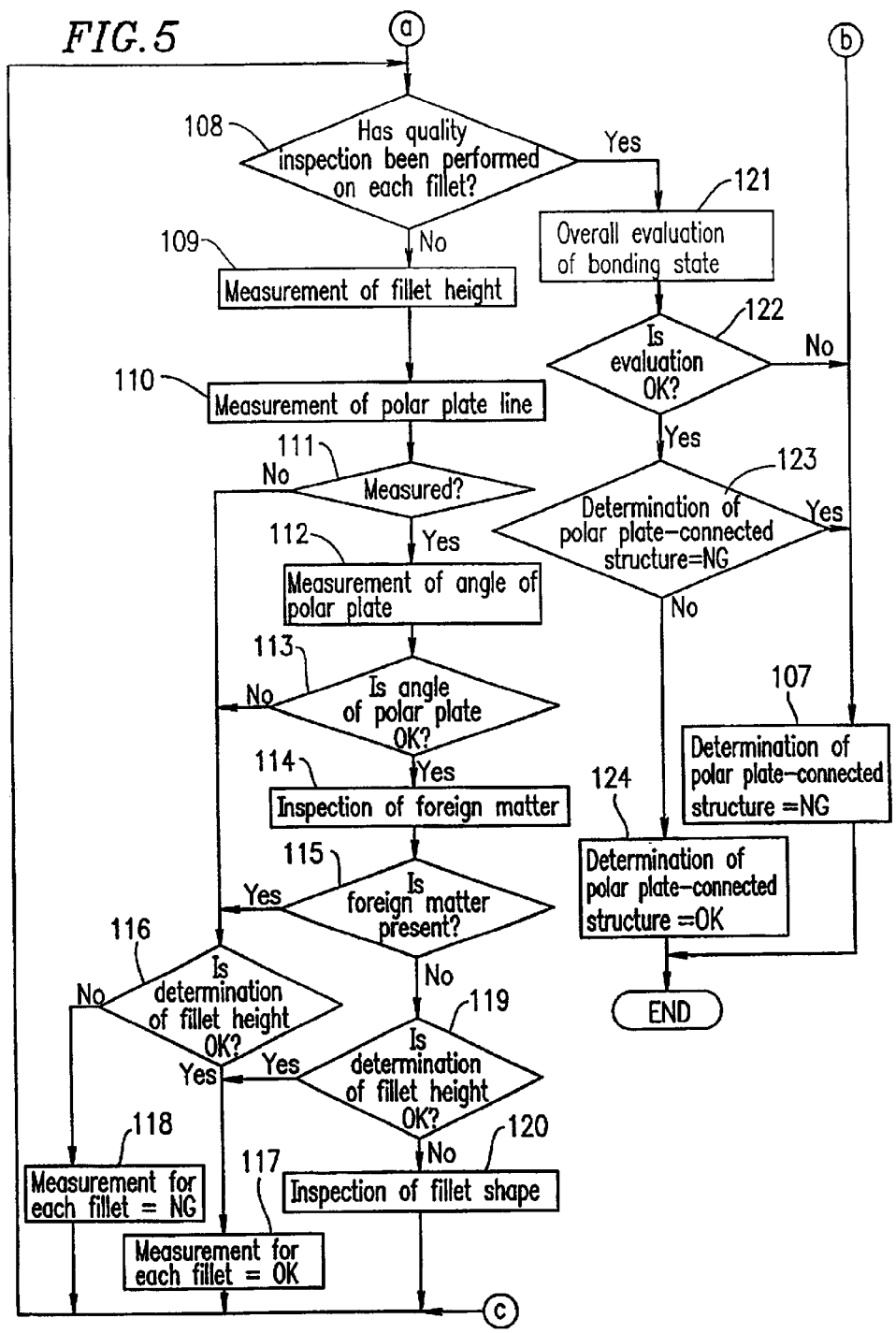

Measurement of difference in height of left and right flanges of power collecting plate Inspection for fillet number Measurement of thickness of polar plate Measurement of fillet height Inspection of fillet shape

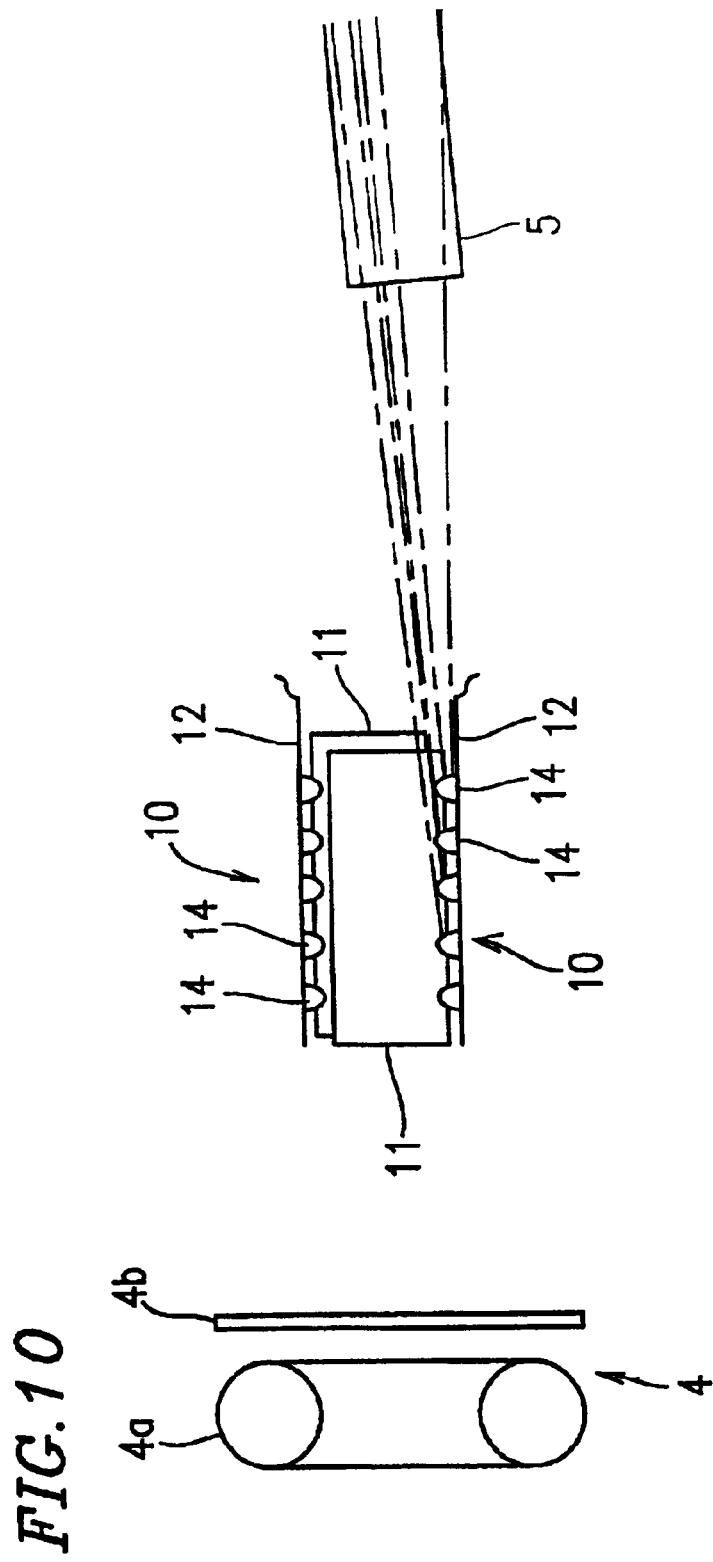

INSPECTION APPARATUS AND METHOD FOR ELECTRODE PLATE-CONNECTED STRUCTURE FOR SECONDARY CELL

BACKGROUND OF THE INVENTION

1. Field of the Invention

The present invention relates to an inspection apparatus for an electrode plate-connected structure for a secondary cell which is used for optically inspecting a connection between each electrode plate and a corresponding one of two power collecting plates included in an electrode plate-connected structure of a sealed-type secondary cell including a plurality of electrode plates connected to a corresponding one of the two power collecting plates, and the present invention further relates to a method for inspecting the same.

2. Description of the Related Art

A sealed-type secondary battery, such as a nickel-cadmium battery, a nickel metal hydride battery, etc., includes an electrode plate-connected structure including a plurality of positive electrode plates and a plurality of negative electrode plates which are laminated such that two adjacent electrode plates have different polarities and a dielectric separator between them and are connected to a corresponding one of two power collecting plates. The electrode plate-connected structure is sealed together with an electrolyte in a thin battery case having a rectangular solid shape. In the electrode plate-connected structure used for a sealed-type secondary cell, a plurality of rectangular plates having the same polarity are placed in parallel to one another at regular intervals on a rectangular power collecting plate. The plurality of rectangular plates having the same polarity are placed perpendicularly to the rectangular power collecting plate and are integrally connected at a plurality of portions along its side edge to the rectangular power collecting plate by brazing, welding, etc.

FIG. 12 is a front view of a primary part of an electrode plate-connected structure 10 formed in the above-described manner which includes a rectangular power collecting plate 12 and a plurality of electrode plates 11 each similarly having a rectangular shape and longitudinal side edges projecting in the same direction.

The plurality of electrode plates 11 having the same polarity are placed in parallel to one another at prescribed intervals on a surface of the power collecting plate 12 along a longitudinal direction of the power collecting plate 12. A plurality of portions along a side edge of each electrode plate 11 placed on the surface of the power collecting plate 12 are bonded to the power collecting plate 12 by brazing, welding, etc. At the junctions of each electrode plate 11 and the power collecting plate 12, a brazing filler metal coating the surface of the power collecting plate 12 is melted so that fillets 14 which are metallic solidified portions of the brazing filler metal are formed on both sides of each electrode plate 11. Each electrode plate 11 is integrally bonded to the surface of the power collecting plate 12 by the fillets 14.

The fillets 14 are basically formed between adjacent pairs of electrode plates 11 and between the two electrode plates 11 placed furthermost from each other in a width direction of the power collecting plate 12 and a flange of the power collecting plate 12 closest to such two electrode plates 11. The fillets 14 fill the corners made between each of electrode plates 11 and the power collecting plate 12. Each fillet 14 formed between the adjacent pairs of electrode plates 11 has a concave shape and a surface which is curved like the figure U.

In the electrode plate-connected structure 10, uniform formation of a fillet 14 at each corner of an electrode plate 11 and the power collecting plate 12 is not readily achieved. There is a possibility that the fillet 14 is not formed at some corners of the electrode plates 11 and the power collecting plate 12 or a possibility that the fillets 14 are not formed into a shape which can securely bond the electrode plates 11 to the power collecting plate 12.

For example, in an area denoted by A in FIG. 12, the fillet 14 is not substantially present on both sides of the electrode plate 11, such that the bonding strength of the electrode plate 11 with respect to the power collecting plate 12 is not sufficient. In an area denoted by B, the fillet 14 is only present on one side of the electrode plate 11. In such a case, when the bonding strength provided by the fillet 14 formed on the side of the electrode plate 11 is sufficient, no problems are caused.

In an area denoted by C, each fillet 14 formed on both sides of the electrode plate 11 does not have a sufficient thickness in the vicinity of the electrode plate 11, so that this electrode plate 11 cannot obtain sufficient bonding strength from each of the fillets 14.

In an area denoted by D, each fillet 14 formed on both sides of the electrode plate 11 has a thickness gradually reduced in a direction away from the electrode plate 11. However, each of the fillets 14 has a sufficient thickness in the vicinity of the electrode plate 11, so that the bonding strength of the electrode plate 11 with respect to the power collecting plate 12 is sufficient and no problems would be caused.

Thus, each of the fillets 14 in the areas denoted by A, B and C of FIG. 12 does not have a shape which provides sufficient bonding strength to the electrode plate 11 with respect to the power collecting plate 12.

When the fillet 14 has a shape shown in the area denoted by A, B or C, the electrode plate 11 is poorly bonded to the power collecting plate 12, so that there arises a possibility that the electrode plate 11 is readily detached from the power collecting plate 12 through impact, for example. Therefore, before the electrode plate-connected structure 10 including electrode plates 11 connected to the power collecting plate 12 is sealed in a battery case, a bonding state of each of the electrode plates 11 with respect to the power collecting plate 12 is inspected.

In the inspection of a bonding state of each of the electrode plates 11 with respect to the power collecting plate 12, it is determined whether or not a bonding state of each of the electrode plates 11 with respect to the power collecting plate 12 is satisfactory, for example, by charging the power collecting plate 12 of the electrode plate-connected structure 10 with electricity and measuring a drop in voltage at a connection between each of the electrode plate 11 and the power collecting plate 12 based on fluctuations in a resistance value caused by poor bonding.

Japanese Laid-Open Publication No. 8-287962 discloses a method for inspecting a bonding state of battery terminals, though such a method cannot be used for directly inspecting a bonding state of each of the electrode plates 11 with respect to the power collecting plate 12. This method uses an acceleration pickup for detecting oscillation caused by a hammer striking the battery terminals of a storage cell in which an electrode plate-connected structure (corresponding to the electrode plate-connected structure 10) is sealed in a battery case and performs a fast Fourier analysis on the detected oscillation. This method can be applied to determining whether or not a bonding state of the electrode plates and a power collecting plate is satisfactory. Such a determination is performed by striking a battery case in which the electrode plate-connected structure 10 is sealed so as to cause oscillation and analyzing the oscillation.

Japanese Laid-Open Publication No. 2000-100465 discloses a method for detecting whether or not a state of a welded portion of a lead of an electrode plate with respect to an encapsulation structure is satisfactory. Such a determination is performed by detecting a displacement when a tensile force is applied to the welded portion of the lead of the electrode plate and the encapsulation structure and comparing absolute values and differences in the displacement caused at the beginning and end of the application of the tensile force to corresponding prescribed values. This method can be applied to determining whether or not a bonding state of a welded portion of the electrode plates and a power collecting plate is satisfactory. Such a determination is based on an amount of displacement detected by applying tensile force to the welded portion of the electrode plates and the power collecting plate.

However, the following problems arise in the above-described methods.

There is a possibility that the method for determining whether or not a bonding state of the electrode plate 11 and the power collecting plate 12 is satisfactory, based on a drop in voltage at each of the fillets 14, cannot securely detect a poorly-bonded fillet 14, even when one is present. The reason for this is that the electrode plate-connected structure 10 used for a sealed-type secondary cell includes a plurality of electrode plates 11 connected to the power collecting plate 12 by means of a plurality of fillets 14, so that when there are few poorly-bonded fillets 14 and most of the fillets 14 are well-bonded, a drop in voltage over all of the fillets 14 is small.

When the electrode plate-connected structure 10 is sealed in a battery case, a plurality of positive electrode plates 11 and a plurality of negative electrode plates 11 are laminated such that two adjacent electrode plates 11 have different polarities and a separator between them. In such a case, even when the battery case is struck, each of the electrode plates 11 is not sufficiently oscillated. Accordingly, when a bonding state of each of the electrode plates 11 and a corresponding one of two power collecting plates 12 is determined by striking the battery case and analyzing oscillation caused by the impact, there arises a problem that accurate detection of a bonding state of each of the electrode plates 11 and the power collecting plate 12 based on the oscillation is not readily provided.

Moreover, in this case, a bonding state of the plurality of electrode plates 11 and the power collecting plate 12 is determined based on an oscillation state of the entire electrode plate-connected structure 10, so that when the number of the poorly-bonded fillets 14 is small, there arises a possibility that the poorly-bonded fillets 14 are not accurately determined.

In the method for inspecting a bonding state by applying a tensile force to a bonded portion and detecting a subsequent displacement of the bonded portion, each of the electrode plate-connected plates 11 is connected at a plurality of connection portions to the power collecting plate 12, so that there arises a problem that it is not possible to determine whether or not a bonding state of each of the electrode plates 11 is satisfactory as to each of the plurality of connection portions.

SUMMARY OF THE INVENTION

According to one aspect of the present invention, there is provided an inspection apparatus for an electrode plate-connected structure for a secondary cell for inspecting each bonding portion of an electrode plate-connected structure for a secondary cell including a plurality of electrode plates which are arranged in parallel to one another at prescribed intervals and are perpendicularly connected to a power collecting plate, the apparatus characterized by including: a lighting section for irradiating light to each of the bonded portions of the plurality of electrode plates and the power collecting plate of the electrode plate-connected structure for a secondary cell; a light receiving section for detecting a projected image of each of the bonded portions based on the light irradiated to the electrode plate-connected structure for a secondary cell by the lighting section; and an evaluation section for evaluating a bonding state of each of the bonding portions based on the projected image of each of the bonded portions detected by the light receiving section.

In one embodiment of the invention, the light receiving section may receive light passing through both sides of each of the electrode plates of the electrode plate-connected structure for a secondary cell.

In another embodiment of the invention, the evaluation section may evaluate a bonding state of each of the bonded portions by measuring a height of a lowest point of each of the bonded portions based on the projected image of each of the bonded portions so as to compare the measured height of the lowest point with a reference value.

In still another embodiment of the invention, the evaluation section may detect a thickness of each of the plurality of the electrode plates based on the projected image of each of the bonded portions.

In still another embodiment of the invention, the evaluation section may detect an inclination state of each of the plurality of the electrode plates based on the projected image of each of the bonded portions.

In still another embodiment of the invention, the evaluation section may evaluate a lowest point of each of the bonded portions based on the projected image of each of the bonded portions and a bonding state of each of the bonded portions based on a position of each of the bonded portions which is in contact with a surface of each of the electrode plates located on opposite sides of each of the bonded portions.

In still another embodiment of the invention, the light receiving section may receive light reflected by each of the bonded portions.

According to another aspect of the present invention, there is provided an inspection method for inspecting an electrode plate-connected structure for a secondary cell by inspecting each bonding portion of an electrode plate-connected structure for a secondary cell including a plurality of electrode plates which are arranged in parallel to one another at prescribed intervals and are perpendicularly connected to a power collecting plate, the method characterized by comprising the steps of: irradiating light to each of the bonded portions of the plurality of electrode plates and the power collecting plate of the electrode plate-connected structure for a secondary cell; detecting a projected image of each of the bonded portions based on the light irradiated to the electrode plate-connected structure for a secondary cell by the lighting section; and evaluating a bonding state of each of the bonding portions based on the projected image of each of the bonded portions detected by the light receiving section.

In one embodiment of the invention, the projected image may be acquired based on light passing through both sides of each of the electrode plates of the electrode plate-connected structure for a secondary cell.

In another embodiment of the invention, the step of evaluating may include evaluating a bonding state of each of the bonded portions by measuring a height of a lowest point of each of the bonded portions based on the projected image of each of the bonded portions so as to compare the measured height of the lowest point with a reference value.

In still another embodiment of the invention, the step of evaluating may include detecting a thickness of each of the plurality of the electrode plates based on the projected image of each of the bonded portions.

In still another embodiment of the invention, the step of evaluating may include detecting an inclination state of each of the plurality of the electrode plates based on the projected image of each of the bonded portions.

In still another embodiment of the invention, the step of evaluating may include evaluating a lowest point of each of the bonded portions based on the projected image of each of the bonded portions and a bonding state of each of the bonded portions based on a position of each of the bonded portions which is in contact with a surface of each of the electrode plates located on opposite sides of each of the bonded portions.

In still another embodiment of the invention, the projected image may be acquired based on light reflected by each of the bonded portions.

Thus, the invention described herein makes possible the advantages of providing an apparatus and a method for inspecting an electrode plate-connected structure for a secondary cell which can accurately and readily evaluate a bonding state in an electrode plate-connected structure for each bonded portion in a quantitative manner.

These and other advantages of the present invention will become apparent to those skilled in the art upon reading and understanding the following detailed description with reference to the accompanying figures.

BRIEF DESCRIPTION OF THE DRAWINGS

FIG. 5 is a flowchart for explaining an operation of the inspection apparatus for an electrode plate-connected structure for a secondary cell according to an embodiment of the present invention.

FIG. 10 is a diagram illustrating a schematic structure of a primary part of an inspection apparatus for an electrode plate-connected structure for a secondary cell according to another embodiment of the present invention.

DESCRIPTION OF THE PREFERRED EMBODIMENTS

Hereinafter, embodiments of the present invention will be described with reference to the drawings.

Figure 1:
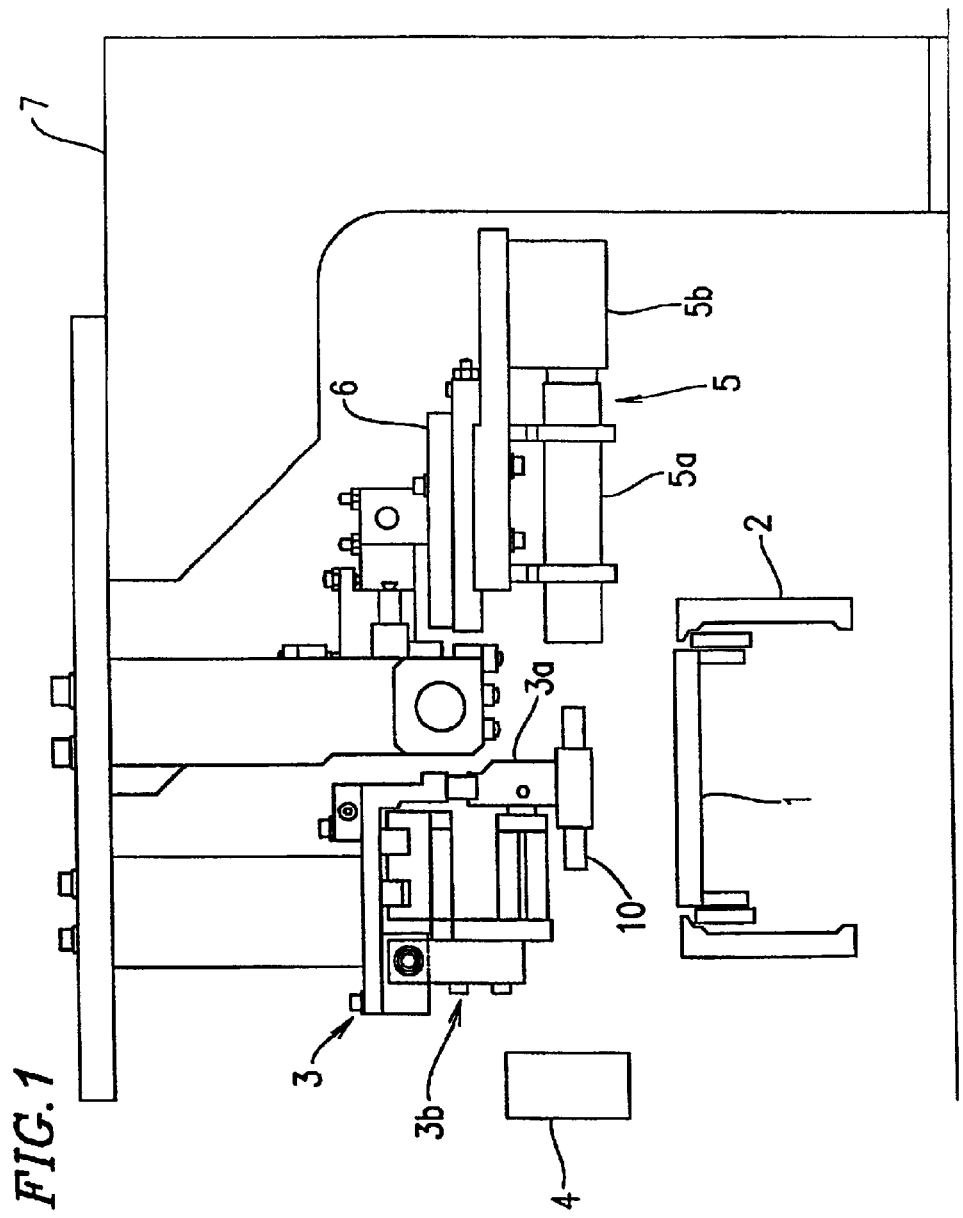
FIG. 1 is a schematic front view of an inspection apparatus for an electrode plate-connected structure for a secondary cell according to an embodiment of the present invention.

FIG. 1 is a front view of an inspection apparatus for an electrode plate-connected structure for a secondary cell according to an embodiment of the present invention.

Figure 12:
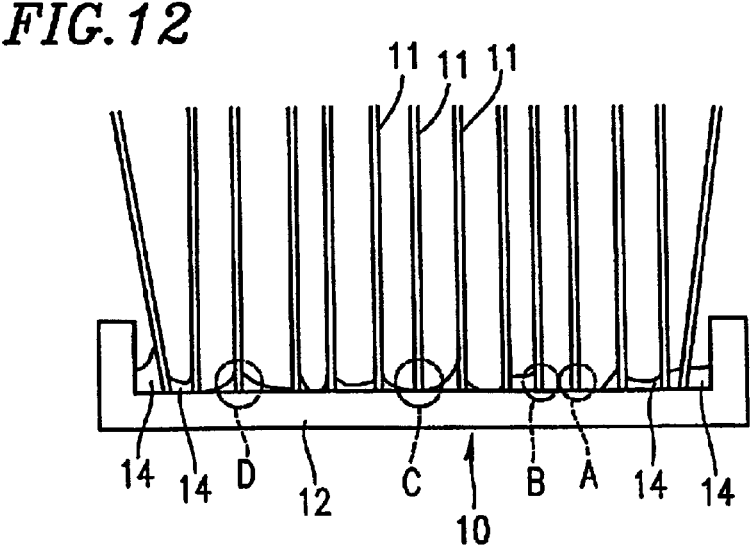
FIG. 12 is a front view of a primary part of an electrode plate-connected structure for a secondary cell.

This inspection apparatus for an electrode plate-connected structure for a secondary cell is used for inspecting the bonding strength of each fillet 14 which are the bonded portions of an electrode plate-connected structure 10 included in a sealed secondary cell as illustrated in FIG. 12. The electrode plate-connected structure 10 includes a plurality of electrode plates 11 having the same polarity placed in parallel to one another at prescribed intervals along a longitudinal direction on a surface of a power collecting plate 12. A plurality of portions along a side edge of each electrode plate 11 placed on the surface of the power collecting plate 12 are bonded to the power collecting plate 12 by brazing, welding, etc. At the junctions of each electrode plate 11 and the power collecting plate 12, a brazing filler metal coating the surface of the power collecting plate 12 is melted so that the fillets 14 which are metallic solidified portions of the brazing filler metal are formed on both sides of each electrode plate 11. Each electrode plate 11 is integrally bonded to the surface of the power collecting plate 12 by the fillets 14.

The sealed-type secondary battery includes a pair of the electrode plate-connected structures 10 which are combined in a laminated manner such that each electrode plate 11 of one of the electrode plate-connected structures 10 is placed between two of the electrode plates 11 of the other electrode plate-connected structure 10, and a dielectric separator is placed between every two adjacent electrode plates 11. The pair of electrode plate-connected structures 10 are sealed together with an electrolyte in a thin battery case having a rectangular solid shape.

The inspection apparatus for an electrode plate-connected structure for a secondary cell according to the present invention is used in conjunction with a secondary cell which includes the pair of electrode plate-connected structures 10 combined with the dielectric separators so as to be sealed in a battery case and detects whether or not a bonding state of the fillets 14, which are the bonded portions of each of the electrode plates 11 of the pair of electrode plate-connected structures 10 and the corresponding power collecting plate 12, is satisfactory.

The inspection apparatus for an electrode plate-connected structure for a secondary cell according to the present invention as shown in FIG. 1 includes: a inspection piece supporting section 3 attached to a frame 7 so as to hold the pair of electrode plate-connected structures 10 in a pre-scribed state, a lighting section 4 placed on one side of the pair of electrode plate-connected structures 10 held by the inspection piece supporting section 3 so as to irradiate the pair of electrode plate-connected structures 10 held in a prescribed state by the inspection piece supporting section 3; and a light receiving section 5 placed opposite to the lighting section 4 with respect to the pair of electrode plate-collected structures 10 held by the inspection piece supporting section 3.

The pair of combined electrode plate-connected structures 10 are conveyed to the inspection apparatus for an electrode plate-connected structure for a secondary cell by a conveyer 2. The pair of electrode plate-connected structures 10 are conveyed by the conveyer 2 in a horizontal direction while they are mounted on a stage 1. After the conveyer 2 conveys the stage 1 to a prescribed position in the inspection apparatus, a lifter (not shown) moves the stage 1 upward in a horizontal state until the pair of the electrode plate-connected structures 10 mounted on the stage 1 reaches an inspection position. When the pair of the electrode plate-connected structures 10 reaches the inspection position, the pair of the electrode plate-connected structures 10 are held by a chuck 3a of the inspection piece supporting section 3.

Figure 2:
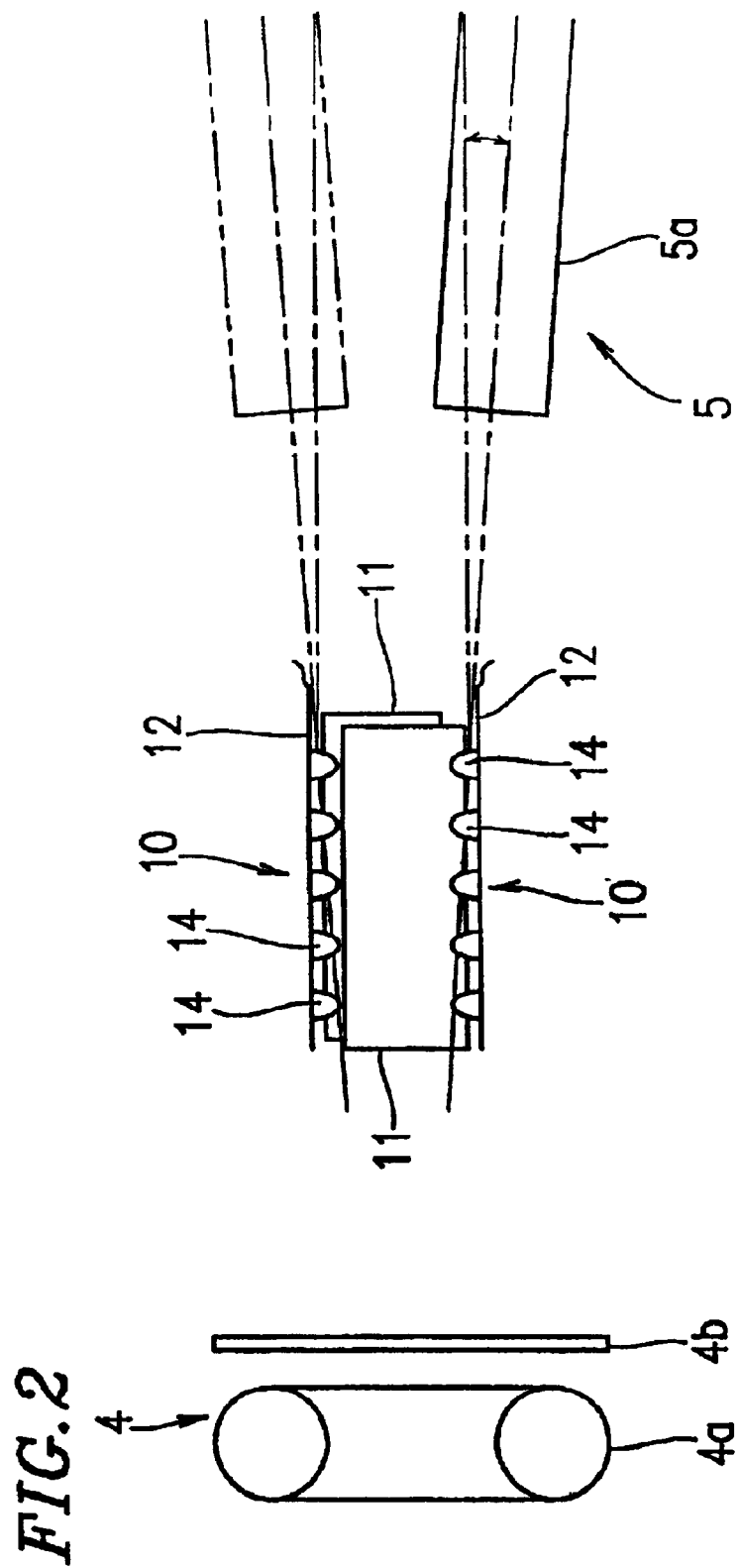
FIG. 2 is a diagram illustrating a schematic structure of a primary part of the inspection apparatus for an electrode plate-connected structure for a secondary cell according to an embodiment of the present invention.

FIG. 2 is a schematic view of the pair of the electrode plate-connected structures 10 held in the inspection position by the chuck 3a. The chuck 3a is held and fixed in the inspection position between the lighting section 4 and the light receiving section 5 such that the respective power collecting plates 12 of the pair of the electrode plate-connected structures 10 are horizontally placed to face away from each other with respect to the fillets 14, and each of the electrode plates 11 is vertical to a direction of light irradiated by the lighting section 4. The inspection piece supporting section 3 is provided with an adjustment mechanism 3b (FIG. 1) which moves the chuck 3a in horizontal and vertical directions and turns the chuck 3a around a prescribed axis so as to place the pair of the electrode plate-connected structures 10 in the inspection position in the above-described manner.

The pair of the electrode plate-connected structures 10 held by the chuck 3a of the inspection piece supporting section 3 is irradiated along the electrode plates 11 with light for inspection by the lighting section 4. The light receiving section 5 includes a telecentric lens 5a placed to receive light irradiated on the pair of the electrode plate-connected structures 10 by the lighting section 4 and a CCD camera 5b (FIG. 1) for receiving light passing through the telecentric lens 5a. In the light receiving section 5, a direction of an optical axis of the telecentric lens 5a and the CCD camera 5b is adjusted by a light receiving section supporting section 6 (FIG. 1) attached to the frame 7.

As illustrated in FIG. 2, the lighting section 4 includes a fluorescent lamp 4a and a white acrylic plate 4b. The lighting section 4 irradiates the pair of the electrode plate-connected structures 10 held in the inspection position with inspection light which is irradiated by the fluorescent lamp 4a and is diffused through the white acrylic plate 4b.

The pair of the electrode plate-connected structures 10 held in the inspection position by the chuck 3a is irradiated with the inspection light which is horizontally incident on each of the electrode plates 11 of the electrode plate-connected structures 10. As a result, the inspection light irradiated by the lighting section 4 passes along a surface of each of the electrode plates 11 and is received by the CCD camera 5b through the telecentric lens 5a of the light receiving section 5. In the CCD camera 5b of the light receiving section 5, an angle of inclination of an optical axis with respect to the power collecting plate 12 which is placed in a horizontal state can be sequentially changed at a slight angle between about 1.5° and about 2.5° so as to sequentially take an image of each of the fillets 14 which are bonded portions of each of the electrode plates 11 of the pair of electrode plate-connected structures 10 and the corresponding power collecting plate 12. Specifically, an image of each of the fillets 14 properly spaced in parallel to the longitudinal direction thereof is sequentially captured.

Figure 3:
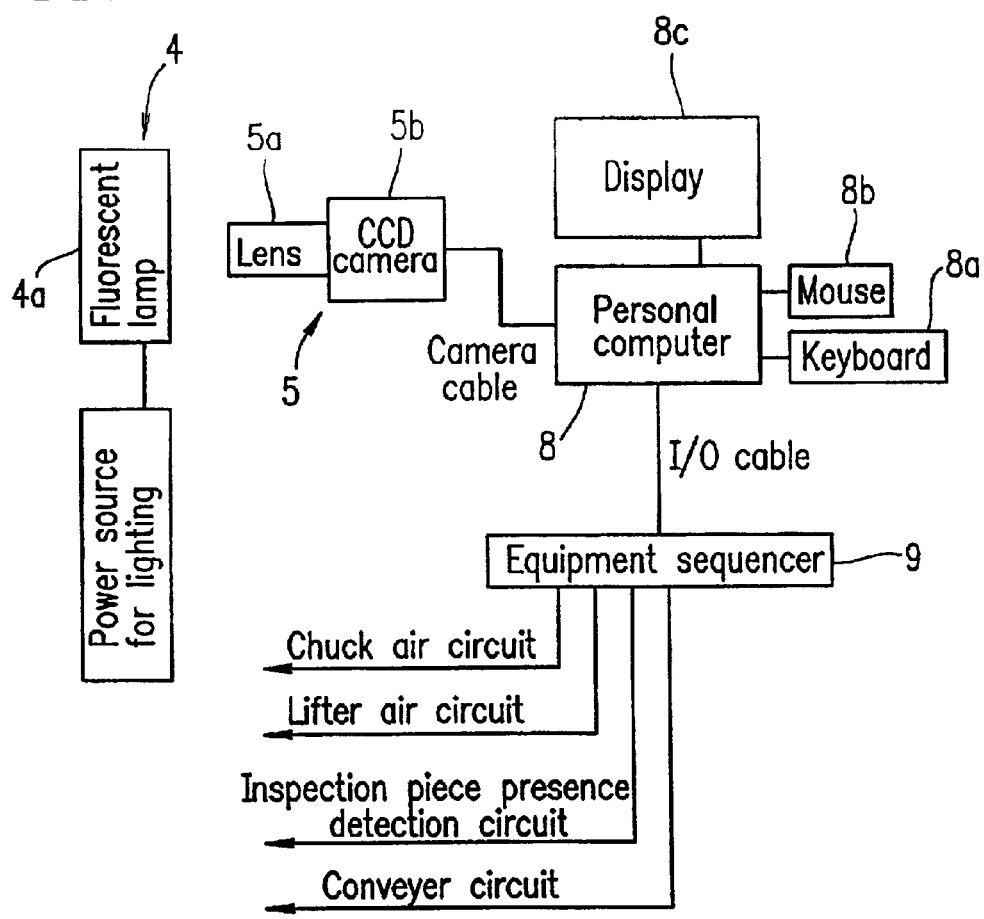
FIG. 3 is a block diagram illustrating an electronic system of the inspection apparatus for an electrode plate-connected structure for a secondary cell according to an embodiment of the present invention.

FIG. 3 is a block diagram illustrating an electronic system of the inspection apparatus for an electrode plate-connected structure for a secondary cell. The CCD camera 5b provided in the light receiving section 5 is controlled by a personal computer 8. The personal computer 8 has a function of acquiring an image projected on the fillet 14 which is detected by the CCD camera 5b of the light receiving section 5 so as to evaluate the bonding strength of each of the fillets 14 of the electrode plates 11 in a quantitative manner using the projected image. The personal computer 8 also controls the conveyer 2, the lifter, the inspection piece supporting section 3, etc., through an equipment sequencer 9 so as to align the pair of the electrode plate-connected structures 10 with the inspection position and fix the pair of the electrode plate-connected structures 10 in place.

The personal computer 8 is connected to a keyboard 8a and a mouse 8b which are used as data input means and is also connected to a display 8c as data representation means.

Referring to a flowchart shown in FIGS. 4 and 5, an operation of the inspection apparatus for an electrode plate-connected structure for a secondary cell having the above-described structure is described below.

When the pair of the electrode plate-connected structures 10 are fixed as an inspection piece in the inspection position in the inspection apparatus for an electrode plate-connected structure for a secondary cell, the inspection apparatus detects where the inspection piece is positioned in an image captured by the CCD camera 5b. The fixed position of the pair of the electrode plate-connected structures 10 (the inspection piece) is corrected in the following manner (step 101). For example, when a lower electrode plate-connected structure 10 of the inspection piece is inspected first, as shown in FIG. 6A, the CCD camera 5b acquires an image in a measurement region 5c corresponding to the power collecting plate 12 and portions of electrode plates 11 in an area above the power collecting plate 12.

As described above, the electrode plate-connected structure 10 is fixed by the chuck 3a of the inspection piece supporting section 3 but there is a slight error in position of the power collecting plate 12 with respect to a predetermined position and an image acquired from the power collecting plate 12 has deviations, inclinations and the like with respect to the predetermined position in directions including upwards, downwards, right and left. Accordingly, it is necessary to detect the position of the power collecting plate 12 in the measurement region 5c and to correct the position so as to decide the position of the power collecting plate 12 in the measurement region 5c. In order to decide the position of the power collecting plate 12 in the measurement region 5c, measurement regions VA are set in the neighborhood of left and right ends, respectively, of the measurement region 5c. In each of the measurement regions VA, a shading from the top to the bottom of an image is calculated. In the image, at a point where a variation in the shading exceeds a reference value, a bright background image on which light is incident directly from the lighting section 4 changes to an image of the power collecting plate 12 which appears to be black, like a shadow, and such a point is determined to be an upper edge of the power collecting plate 12. In this manner, the upper edges of the power collecting plate 12 are decided at left and right side edges.

Figure 6A:
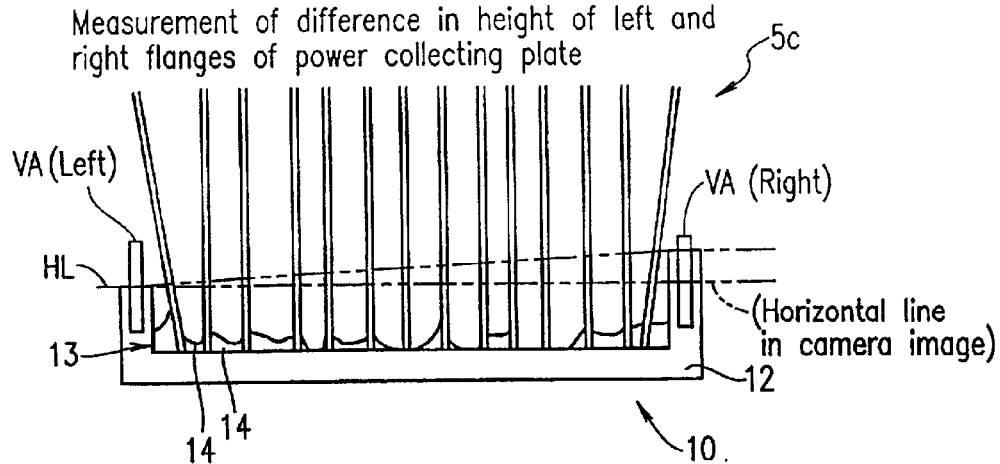
FIG. 6A is a view for explaining inspection of an electrode plate-connected structure performed by the inspection apparatus for an electrode plate-connected structure for a secondary cell according to an embodiment of the present invention.

Next, as illustrated in FIG. 6A, a reference line HL is set so as to run between the upper edges of the power collecting plate 12. The following process is performed based on the reference line HL rather than coordinates on a screen which uses a horizontal line on the screen as a reference. The use of the reference line HL eliminates effects caused by deviations, inclinations and the like of the electrode plate-connected structure 10 on the measurement region 5c.

Figure 4:
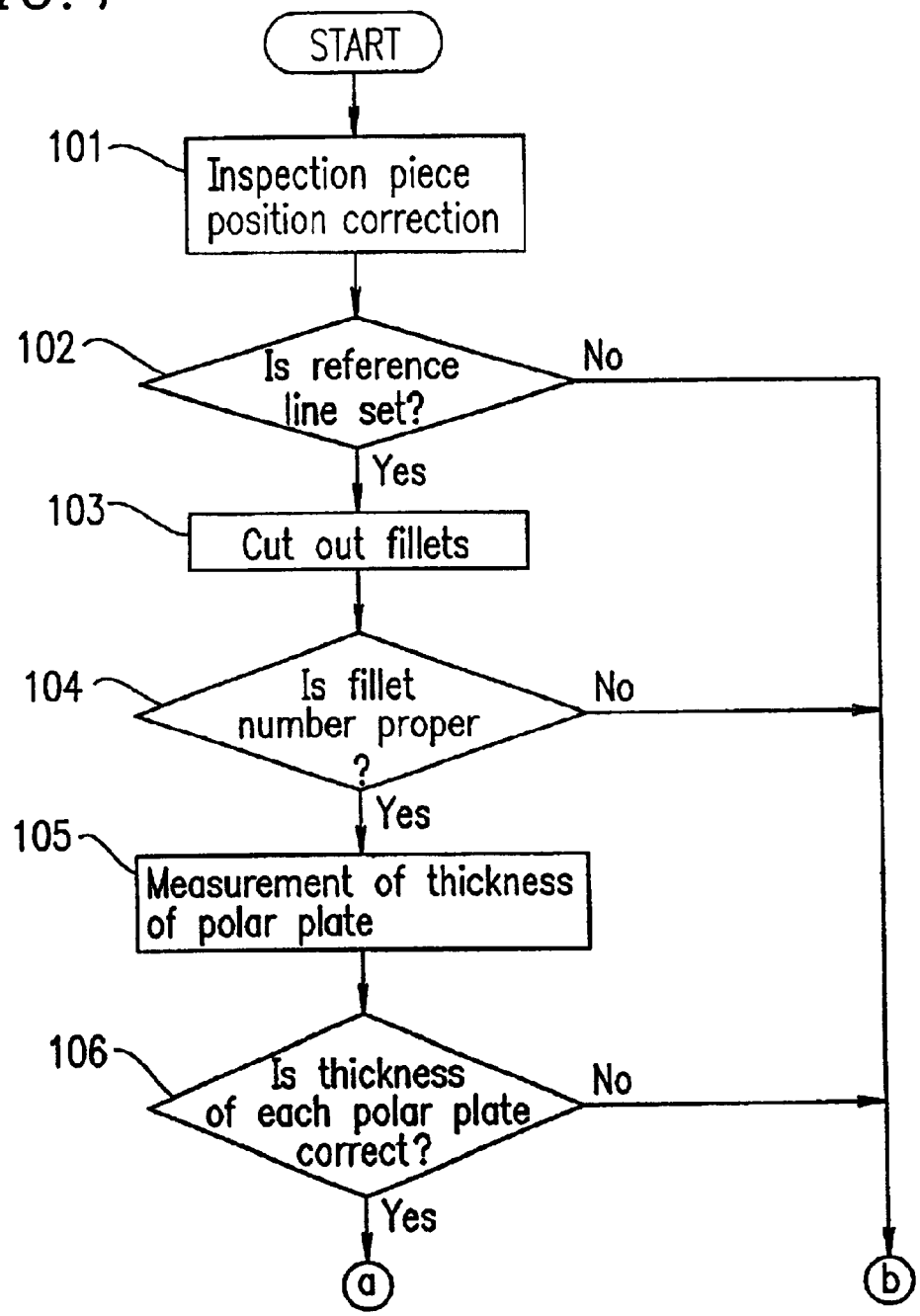
FIG. 4 is a flowchart for explaining an operation of the inspection apparatus for an electrode plate-connected structure for a secondary cell according to an embodiment of the present invention.

In the above-described manner, when the position of the electrode plate-connected structure 10 is corrected, whether or not the reference line HL is set is confirmed (step 102 of FIG. 4). When the setting of the reference HL is not confirmed, the process proceeds to step 107 (FIG. 5), and the electrode plate-connected structure 10 for inspection is determined to be immeasurable (NG). The immeasurability is considered to be caused by large deviations at the time the chuck 3a chucks the electrode plate-connected structure 10, incapability of accurate detection of the upper edges of the power collecting plate 12 due to deformation, etc., of the power collecting plate 12, and so on. When the setting of the reference line HL is confirmed, the process proceeds to step 103.

Figure 6B:
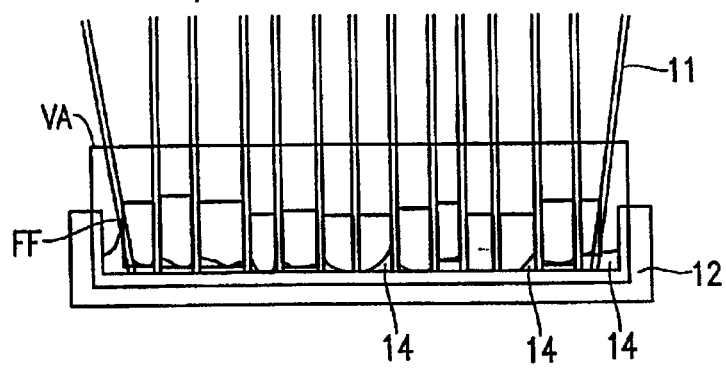
FIG. 6B is a view for explaining inspection of an electrode plate-connected structure performed by the inspection apparatus for an electrode plate-connected structure for a secondary cell according to an embodiment of the present invention.

At step 103, the number of all of the fillets 14 located in a plane including the reference line HL perpendicular to all of the electrode plates 11 in the electrode plate-connected structure 10 is measured based on the image captured by the CCD camera 5b. In this case, as illustrated in FIG. 6B, in a region within the plane including all of the fillets 14 in the image captured by the CCD camera 5b, a range extending from the reference line HL downward to a certain distance is set as the measurement region VA. In the measurement region VA which is set as described above, a rectangular circumscribed with a bright area which is a irradiated portion is extracted between each of the electrode plates 11. After the circumscribed rectangles located at left and right sides of the measurement region VA are removed, a lower half (50%) of each of the circumscribed rectangles which constitute bright areas is selected. In this case, when the lower parts of adjacent circumscribed rectangles overlap each other, such rectangles are merged together. The rectangle selected in this manner is set as a cut-out frame FF of the fillets 14. The number of the fillets 14 in the plane including the reference line HL perpendicular to the power collecting plate 12 is calculated based on the number of the cut-out frames FF set in the above-described manner.

Once the number of the fillets 14 of the electrode plate-connected structure 10 in the plane including the reference line HL perpendicular to the power collecting plate 12 is measured at step 103, the process proceeds to step 104 and it is determined whether or not the number of the fillets 14 is proper. That is, when the number of the fillets 14 is equal to or more than the number of the electrode plates 11 of the electrode plate-connected structure 10 and is equal to or lower than twice the number of the electrode plates 11, the number of the fillets 14 is determined to be proper. At step 104, when the number of the fillets 14 is determined not to be proper, the process proceeds to step 107 and the electrode plate-connected structure 10 is determined to be inferior (NG). When the number of the fillets 14 is determined to be proper, the process proceeds to step 105.

Figure 6C:
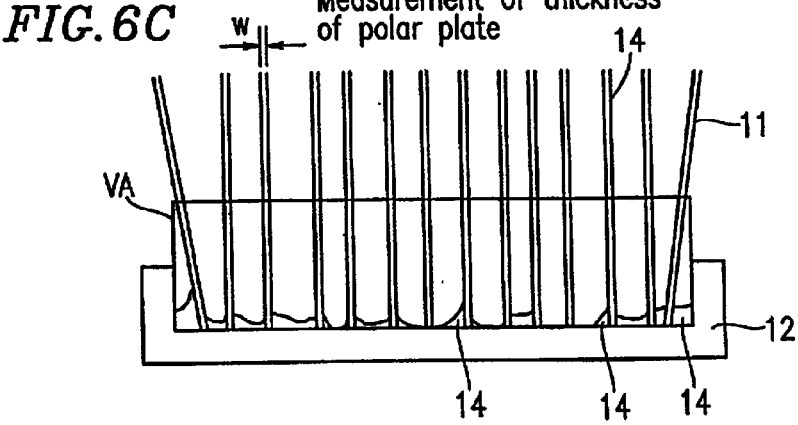
FIG. 6C is a view for explaining inspection of an electrode plate-connected structure performed by the inspection apparatus for an electrode plate-connected structure for a secondary cell according to an embodiment of the present invention.

At step 105, as shown in FIG. 6C, a thickness W of each of the electrode plates 11 of the lower electrode plate-connected structure 10 is measured. In order to measure the thickness W of each of the electrode plates 11, at first, the measurement region VA including the reference line HL and all of the electrode plates 11 is measured, and coordinates of a point of white to black variation and a point of black to white variation are measured from a leftmost electrode plates 11 in the measurement region VA. The points of white to black variation and black to white variation are paired (hereinafter, referred to as an "edge pair"). By calculating a distance between each edge pair, the thickness W of each electrode plate 11 is measured. The thickness W of each electrode plate 11 is sequentially measured from the electrode plate 11 located on the left side on an imaging screen of the CCD camera 5b.

Once the thickness W is measured with respect to each of the electrode plates 11 in the electrode plate-connected structure 10 at step 105, the process proceeds to step 106 and whether or not the thickness W is correct (i.e., whether or not the thickness W is in a tolerable range) with respect to each of the electrode plates 11 having the measured thickness W is determined. When the thickness W of each of the electrode plates 11 is measured, curvature of each electrode plate 11, inclination of each electrode plate 11 toward the power collecting plate 12, and the like are also measured based on an image of the measurement region VA and whether the curvature and inclination of each electrode plate 11 are in respective tolerable ranges is determined. When the thickness W, curvature, or inclination of the electrode plates 11 exceeds a respective reference value, the process proceeds to step 107 and the electrode plate-connected structure 10 including such an electrode plate 11 is determined to be inferior (NG).

When the thickness W, curvature, or inclination of each of the electrode plates 11 is in a respective tolerable range, a quality inspection is performed on each of fillets 14 of the lower electrode plate-connected structure 10 based on the flowchart shown in FIG. 5.

In the quality inspection for each of the fillets 14 of the electrode plate-connected structure 10, at step 108 of FIG. 5, whether the quality inspection has been performed on each of the fillets 14 is determined. At step 109, a height of each of the fillets 14 on which the quality inspection has not been performed is measured. For example, a height of each of the fillets 14 is sequentially measured from a leftmost fillet 14 in the image captured by the CCD camera 5b.

Figure 7A:
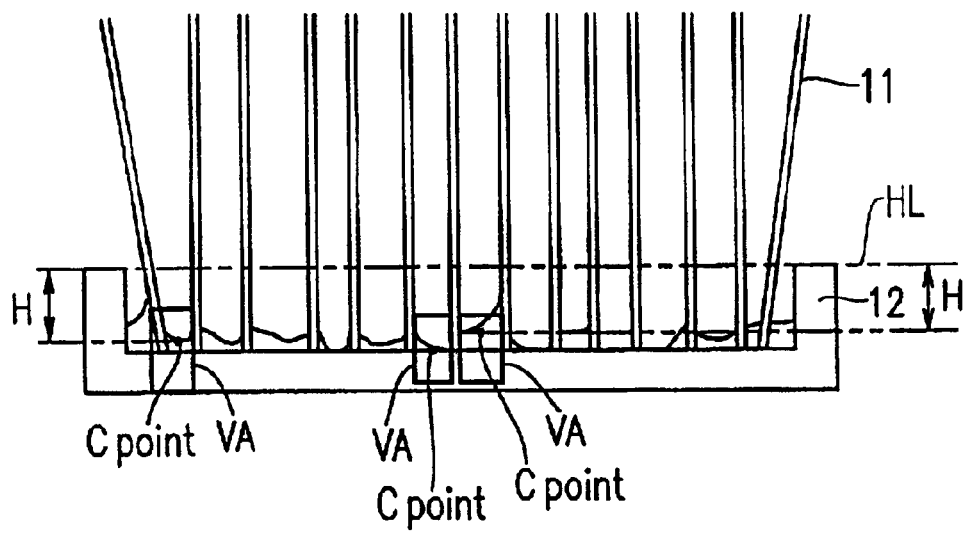
FIG. 7A is a view for explaining inspection of an electrode plate-connected structure performed by the inspection apparatus for an electrode plate-connected structure for a secondary cell according to an embodiment of the present invention.

In this case, as illustrated in FIG. 7A, in the image captured by the CCD camera 5b, each region where the fillets 14 are to be measured is set as a measurement region VA. In the measurement region VA, a point of black to white variation is measured on the screen from the bottom to the top of the image and a lowest point C of the fillet 14 is measured. A distance between the reference line HL and the measured lowest point C is referred to as a height representation distance H of the fillet 14.

The height representation distance H of the fillet 14 measured in the above-described manner is compared to a range of reference values. When the measured height representation distance H of the fillet 14 is within the range of reference values, the measured height representation distance H of the fillet 14 is determined to be proper.

When the fillet 14 is made by brazing, the height representation distance H from the reference line HL to the lowest point C of the fillet 14 represents blazing quantity. When the height representation distance H is great and brazing quantity is small, the bonding strength of the electrode plate 11 with respect to the power collecting plate 12 is not sufficient. When a height representation distance H of each of the fillets 14 provided on both sides of one of the electrode plates 11 is large and the bonding strength provided by each of the fillets 14 is not sufficient, the bonding strength of the one of the electrode plates 11 with respect to the power collecting plate 12 is determined not to be sufficient (NG). When a height representation distance H of only one of the fillets 14 provided on both sides of the one of the electrode plates 11 is large and blazing quantity of the fillet 14 is not sufficient, if the blazing quantity of the fillet 14 provided on the other side of the one of the electrode plates 11 is sufficient, the bonding strength of the one of the electrode plates 11 with respect to the power collecting plate 12 is determined to be sufficient (OK).

When the measured height representation distance H of the fillet 14 is out of the range of reference values, a height representation distance H of the other fillet 14 adjacent to the fillet 14 having the measured height representation distance H is measured. When the measured height representation distance H of the adjacent fillet 14 is lower than a preset reference value, an electrode plate 11 bonded to the power collecting plate 12 between the pair of adjacent fillets 14 is considered to have sufficient bonding strength with respect to the power collecting plate 12, and thus the height of the adjacent fillet 14 is determined to be proper.

In the above-described manner, when the height of the adjacent fillet 14 is determined to be proper at step 109, the process proceeds to step 110 and an electrode plate line which runs along a surface of the electrode plate in contact with the adjacent fillet 14 is measured from the image captured by the CCD camera 5b. In order to measure the electrode plate line, at first, an edge where white to black or black to white variation in left and right directions occurs is detected at top and bottom ends of the screen of the measurement region VA used for determining the thickness W of the electrode plate 11. Coordinates of a pair of edges where white to black variation occurs at upper and lower ends and a pair of edges where black to white variation occurs at upper and lower ends are measured. The line running between the coordinates of the measured pairs is called "the electrode plate line".

When the electrode plate line for the electrode plates 11 is measured in step 110, the process proceeds to step 111 and whether the electrode plate line of the electrode plate 11 is measured is confirmed. When the measurement of the electrode plate line is not confirmed, the process proceeds to step 116.

At step 116, whether the determination result of the measured height of the fillet 14 is proper is confirmed again. When the measured height is proper, the process proceeds to step 117 and the bonding strength of the fillet 14 is determined to be satisfactory (OK). When the determination result of the measured height of the fillet 14 is not proper, the process proceeds to step 118 and the bonding strength of the fillet 14 is determined to be unsatisfactory (NG).

Figure 7B:
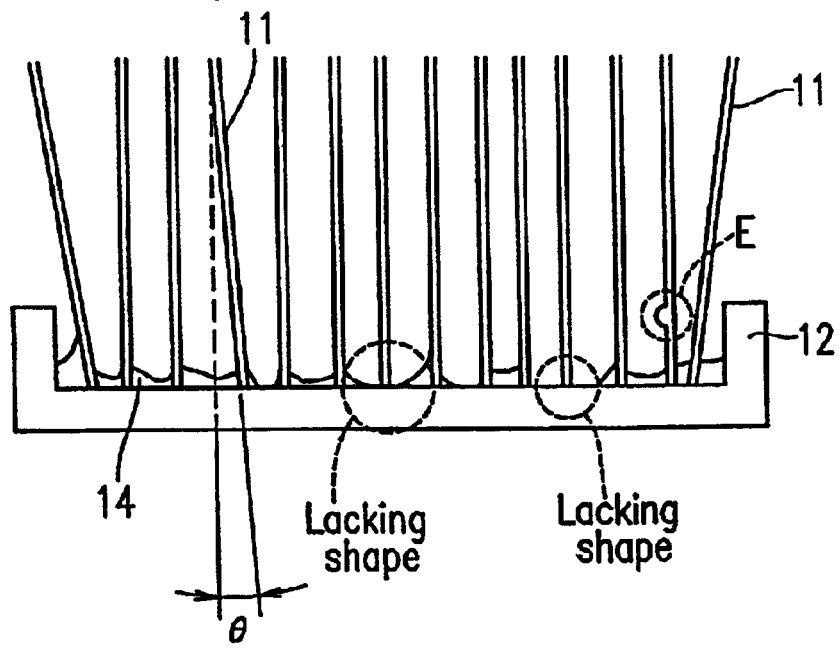
FIG. 7B is a view for explaining inspection of an electrode plate-connected structure performed by the inspection apparatus for an electrode plate-connected structure for a secondary cell according to an embodiment of the present invention.

When the measurement of the electrode plate line of the electrode plate 11 in contact with a designated fillet 14 is confirmed at step 111, the process proceeds to step 112. At step 112, as illustrated in FIG. 7B, an angle of inclination $\theta$ of the electrode plate 11 with respect to a line perpendicular to the reference line HL is measured based on the measured electrode plate line of the electrode plate 11. When the angle of inclination $\theta$ of the electrode plate 11 is measured at step 112, the process proceeds to step 113 and whether or not the measured angle of inclination $\theta$ of the electrode plate 11 is within a tolerable range is determined.

When the measured angle of inclination $\theta$ of the electrode plate 11 is out of the tolerable range, the process proceeds to step 116 and, as described above, whether the determination result of the measured height of the fillet 14 is proper is confirmed again. When the measured height of the fillet 14 is determined to be proper, the process proceeds to step 117 and the bonding strength of the fillet 14 is determined to be satisfactory (OK). When the determination result of the measured height of the fillet 14 is not proper, the process proceeds to step 118 and the bonding strength of the fillet 14 is determined to be unsatisfactory (NG).

When the measured angle of inclination of the electrode plate 11 is within the tolerable range at step 113, the process proceeds to step 114. At step 114, whether or not foreign matter is present on a surface of the electrode plate 11 is determined based on the measured electrode plate line of the electrode plate 11. In order to determine whether foreign matter is present on a surface of the electrode plate 11, a fringe line of the electrode plate 11 is extracted by connecting points of black to white variation in left and right directions in a range extending upward and downward at a prescribed distance from the reference line HL. When the extracted fringe line of the electrode plate 11 is away from the electrode plate line by more than a predetermined reference value, foreign matter is determined to be present on a surface of the electrode plate 11.

In this case, as illustrated in FIG. 7B, when foreign matter E is present on a surface of the electrode plate 11, the process returns to the above-described step 116, and again, the measured height of the fillet 14 is determined to be proper. When foreign matter is not present, the process proceeds to step 119.

At step 119, as in a similar manner to step 116, whether the determination result of the measured height of the fillet 14 is proper is determined. If it is proper, the process proceeds to step 117, and the bonding strength of the fillet 14 is determined to be satisfactory (OK).

When the fillet 14 is determined not to be proper based on the measured height of the fillet 14 at step 119, specifically, when there are no problems as to the angle of inclination $\theta$ of the electrode plate 11 and presence of foreign matter, the lowest point C of the fillet 14 is low, and the thickness of blazing of the fillet 14 is determined not to be sufficient, the process proceeds to step 120. At step 120, a shape of the fillet 14 is further inspected in detail so as to determine whether the bonding strength of the fillet 14 is sufficient.

Figure 8:
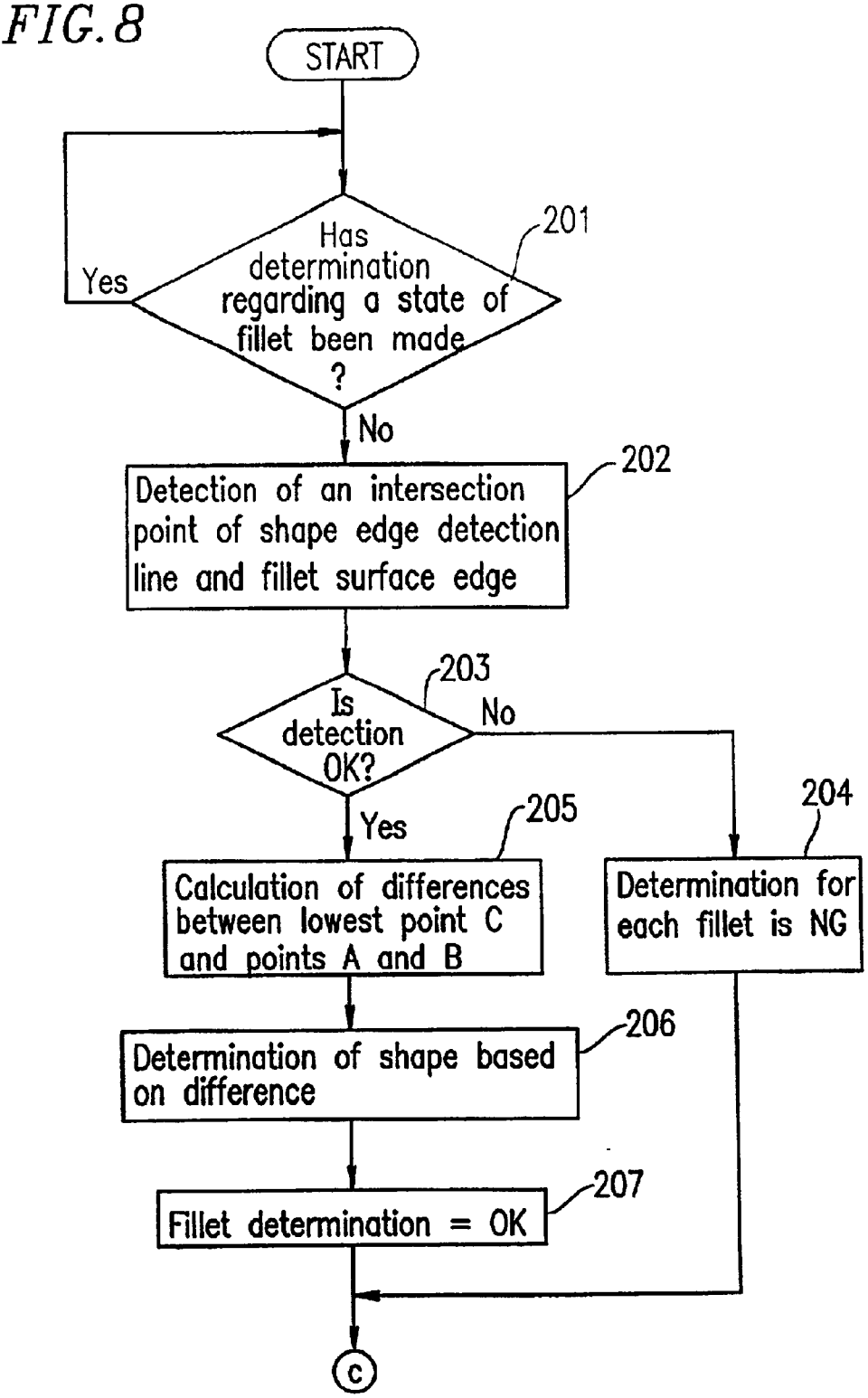
FIG. 8 is a flowchart showing a subroutine for explaining an operation of the inspection apparatus for an electrode plate-connected structure for a secondary cell according to an embodiment of the present invention.

FIG. 8 is a flow chart showing the step of inspecting a shape of the fillet 14 which is performed at step 120 shown in FIG. 5. At step 201 shown in FIG. 8, whether either of the determinations of whether the selected fillet 14 is satisfactory or unsatisfactory has not been made is confirmed. When the confirmation that either of such determinations has not been made is provided, the process proceeds to step 202, and a position where the fillet 14 is in contact with an electrode plate 11 on each side of the fillet 14 is detected.

Figure 9:
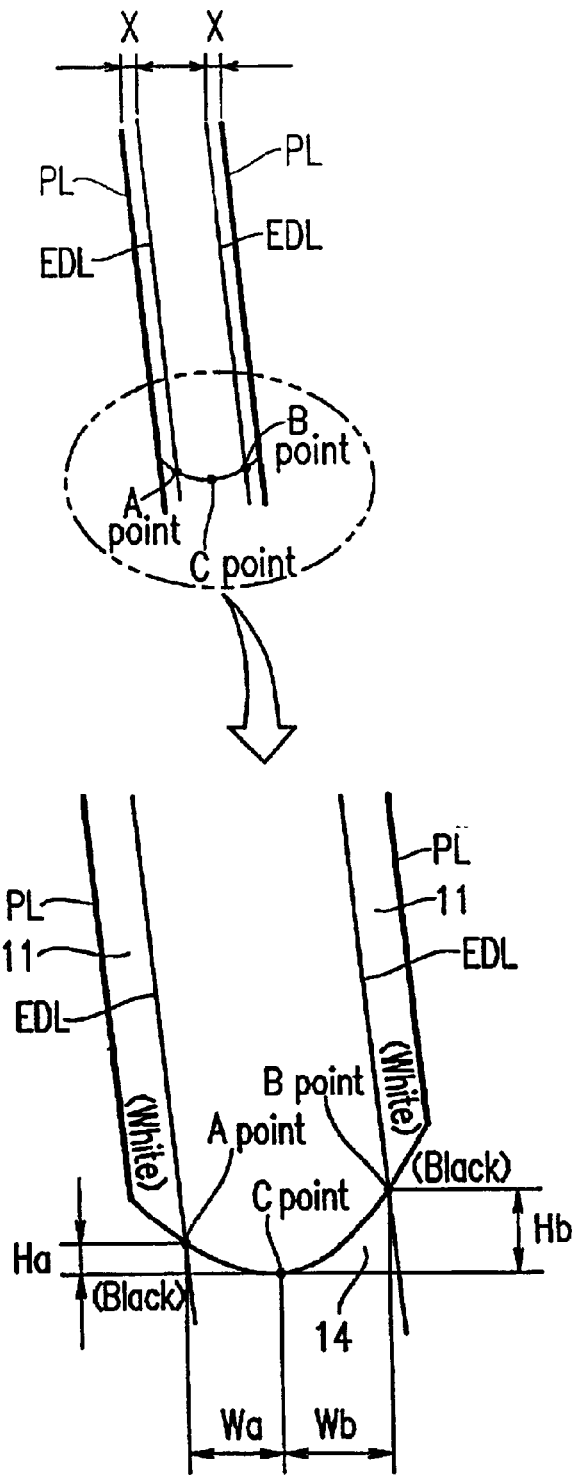
FIG. 9 is a view for explaining inspection of an electrode plate-connected structure performed by the inspection apparatus for an electrode plate-connected structure for a secondary cell according to an embodiment of the present invention.

FIG. 9 illustrates an enlarged portion of the fillet 14 which is in contact with the electrode plates 11 on both sides of the fillet 14. At first, shape edge detection lines EDL are set such that each of the lines EDL is in parallel to and in a prescribed distance away from a corresponding electrode plate line PL which is a surface line of each of the electrode plates 11 located at opposite sides of the fillet 14. Each of the shape edge detection lines EDL is set so as to be outside of each of the electrode plate lines PL with respect to the respective electrode plate 11 and to be away from each of the electrode plate lines PL at a distance X preset by a predetermined parameter. On each edge shape detection line EDL, edges where black to white variation occurs along the lines EDL from the bottom of the screen upwards are referred to as edge points A and B.

When each of the edge points A and B is detected at step 202 (FIG. 8), the detection of the edge points A and B is confirmed at step 203. When the edge points A and B are not detected, the process proceeds to step 204, and determination that the fillet 14 is not satisfactory (NG) is established.

When the detection of the edge points A and B is confirmed at step 203, the process proceeds to step 205 and a relative relationship between the edge points A and B and the lowest point C on the surface of the fillet 14 is calculated. It should be noted that the lowest point C has already been measured together with the height of the fillet 14 (at step 109 of FIG. 5).

In this case, coordinates of the edge points A and B are represented as (Xa, Ya) and (Xb, Yb), respectively. By using coordinates (Xc, Yc) of the lowest point C of the surface of the fillet 14 calculated at the time of the measurement of the fillet 14, respective differences Ha and Hb in height between the edge points A and B and the lowest point C are respectively calculated by the following expressions (1) and (2) and respective distances Wa and Wb in a direction X between the lowest point C and the edge points A and B are respectively calculated by the following expressions (3) and (4).

$$Ha = Ya - Yc \quad (1)$$

$$Hb = Yb - Yc \quad (2)$$

$$Wa = Xc - Xa \quad (3)$$

$$Wb = Xb - Xc \quad (4)$$

When the respective differences Ha and Hb in height between the edge points A and B and the lowest point C and the respective distances Wa and Wb in a direction X between the lowest point C and the edge points A and B are calculated, the process proceeds to step 206 so as to determine a shape of the fillet 14. Specifically, the fillets 14 are classified into the following types: (1) the differences Ha and Hb in height exceed a reference value; (2) the distances Wa and Wb in a direction X exceed a reference value; and (3) the differences Ha and Hb in height satisfy a reference value and the distances Wa and Wb in a direction X satisfy a reference value.

Since each of the differences Ha and Hb in height between the edge points A and B and the lowest point C of the fillet 14 exceeds a reference value, the fillet 14 rises to a sufficient height at the edge points A and B on opposite sides of the fillet 14, so that the bonding strength of the fillet 14 is determined to be sufficient. Moreover, since each of the distances Wa and Wb in the horizontal direction (direction X) between the lowest point C and the edge points A and B exceeds a reference value, the lowest point C of the fillet 14 is not located closer to either side of the electrode plates 11 and is located sufficiently away from each of the electrode plates 11, so that the bonding strength of the fillet 14 is determined to be sufficient.

Accordingly, in the case where the fillet 14 satisfies at least one of the following conditions of: (1) the differences Ha and Hb in height between the edge points A and B and the lowest point C of the fillet 14 exceed a reference value; and (2) the distances Wa and Wb in a direction between the edge points A and B and the lowest point C of the fillet 14 exceed a reference value, even if the lowest point C of the fillet 14 is not sufficiently high, a shape of the fillet 14 provides sufficient bonding strength to support the electrode plates 11 on each side of the fillet 14, so that the fillet 14 is determined to be satisfactory (OK) at step 207.

In this manner, the inspection of a shape allows the detection of the fillets 14 having the poor bonding strength, as denoted by A and C in FIG. 12. Moreover, each pair of fillets 14 has a shape as denoted by D in FIG. 12 in which the fillet 14 rises in a portion close to one of two adjacent electrode plates 11 located on opposite sides of the fillet 14. When each of the pair of the fillets 14 has such a shape, the electrode plate 11 supported between the pair of the fillets 14 has sufficient bonding strength with respect to the power collecting plate 12, and thus it is unnecessarily determined to be poorly-bonded.

In the above-described manner, when the determinations whether or not one of the fillets 14 is satisfactory in height and shape are completed, the process returns to step 108 shown in FIG. 5. When the inspection for all of the fillets 14 is not completed, steps 109 through 120 are repeated, so that all of the fillets 14 located in a plane perpendicular to the power collecting plate 12, i.e., all of the fillets 14 arranged along a width direction of the power collecting plate 12, are inspected in terms of the bonding strength.

When the inspection for the bonding strength of each of the fillets 14 in the plane perpendicular to the power collecting plate 12 is completed, the bonding strength of each of the fillets 14 located in a plane adjacent to the plane perpendicular to the power collecting plate 12 is inspected. For example, when the inspection for the bonding strength of all of the fillets 14 closest to the light receiving section 5 which are arranged in the width direction of the power collecting plate 12 is completed, the bonding strength of all of the fillets 14 which are arranged in the width direction of the power collecting plate 12 and which are adjacent and located on the far side of the fillets 14 closest to the light receiving section 5 is inspected.

When the completion of the inspection of all of the fillets 14 in the lower electrode plate-connected structure 10 is confirmed at step 108 (FIG. 5), the process proceeds to step 121. At step 121, an overall evaluation is performed on the electrode plate-connected structure 10 based on the determination of whether or not each of the fillets 14 of the electrode plate-connected structure 10 are satisfactory. For example, the overall evaluation is performed based on the determination whether a ratio of the fillets 14 determined to be satisfactory to all of the fillets 14 in the electrode plate-connected structure 10 reaches a prescribed reference ratio.

At step 122, when the overall evaluation of the electrode plate-connected structure 10 is satisfactory (OK), whether there is no determination that the overall evaluation of the electrode plate-connected structure 10 is unsatisfactory is confirmed at step 123, so that the overall evaluation of the electrode plate-connected structure 10 is determined to be satisfactory (OK) at step 124. When the overall evaluation of the electrode plate-connected structure 10 is unsatisfactory (NG) at step 122, the electrode plate-connected structure 10 is determined to be unsatisfactory (NG) at step 107.

In the above-described manner, when the inspection of the lower electrode plate-connected structure 10 of two electrode plate-connected structures 10 combined as an inspection piece is completed, the light receiving section 5 is moved from a position indicated by the solid line shown in FIG. 2 to a position indicated by the chained dotted line and inspection of the upper electrode plate-connected structure 10 is performed in a similar manner to the inspection of the lower electrode plate-connected structure 10.

In the inspection apparatus for an electrode plate-connected structure for a secondary cell according to the present invention, the electrode plate-connected structure 10 which includes a proper number of the fillets 14 and electrode plates 11 each having a proper thickness W is inspected such that a height of each of the fillets 14, an angle θ of inclination of each of the electrode plates 11, and whether or not foreign matter is attached on the electrode plates 11 are determined in a position of each of the fillets 14 provided to each of the electrode plates 11. Even in the case where there are problems as to at least either of the angle of inclination θ of the electrode plate 11 and presence of foreign matter, when height of the lowest point C of a fillet 14 is proper, the bonding strength of the fillet 14 is determined to be satisfactory. Even in the case where there are no problems as to either of the angle of inclination θ of the electrode plate 11 and presence of foreign matter, when a height of the lowest point C of a fillet 14 is not proper, whether or not the bonding strength of the fillet 14 is satisfactory is determined based on a shape of the fillet 14.

As described above, the inspection apparatus for an electrode plate-connected structure for a secondary cell according to the present invention can quantitatively evaluate a bonding state of each of the electrode plates 11 and the power collecting plate 12 for each of the fillets 14 provided to the electrode plates 11 from a projected image of each of the fillets 14 in the electrode plate-connected structure 10. The inspection apparatus according to the present invention can also accurately inspect the bonding strength of each of the fillets 14.

Since whether or not the bonding strength of the electrode plates 11 and the fillets 14 are satisfactory are determined based on an external form of each of the electrode plates 11 and fillets 14, the bonding strength of the electrode plates 11 and the fillets 14 can be readily determined without using exclusive hardware for image processing, a high-speed CPU, or the like. When the bonding strength of each of the fillets 14 is determined by pattern matching, a long period of time is taken for the determination since the number of the fillets 14 is large and the fillets 14 significantly lack uniformity in shape. Moreover, there is a problem that a load of the CPU is increased by calculations. However, the inspection apparatus for an electrode plate-connected structure for a secondary cell according to the present invention does not have such problems.

In the above-described embodiment, in order to inspect an external form of each of the fillets 14, inspection light passing through both sides of each of the electrode plates 11 is used. This allows an external form of each of the fillets 14 to be accurately detected even when the electrode plate-connected structure 10 includes a plurality of electrode plates 11 arranged in parallel to one another at narrow intervals, an external shape of each of the fillets 14 is accurately detected. Moreover, a shape of each of the fillets 14 provided at corresponding positions in the longitudinal direction of each of the electrode plates 11 can be concurrently detected, so that efficiency of inspection is significantly improved.

In the above-described embodiment, the lighting section 4 irradiates the light receiving section 5 with light passing through the pair of electrode plate-connected structure 10. However, as illustrated in FIG. 10, the light receiving section 5 may receive light reflected by each of the fillets 14 of the electrode plate-connected structure 10.

Figure 11A:
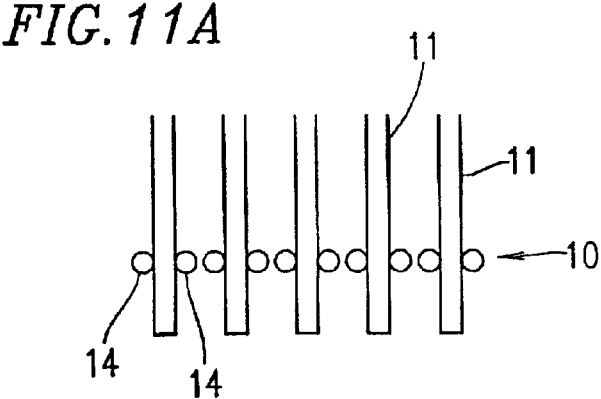
FIG. 11A is a diagram for explaining that a high luminance image is acquired for each fillet when a satisfactory fillet is provided to each side of all of electrode plates.
Figure 11B:
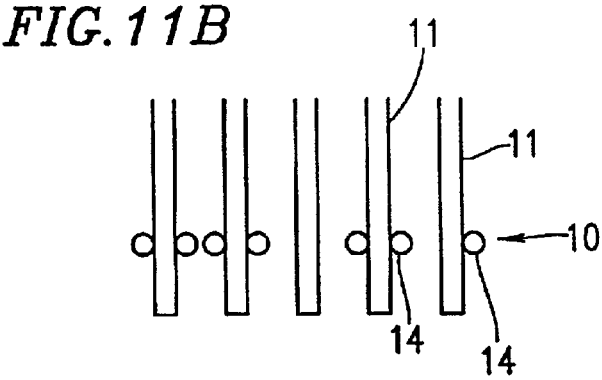
FIG. 11B is a diagram for explaining that a high luminance image cannot be seen at a region where a fillet is absent when a satisfactory fillet is not provided to each side of all of the electrode plates.

In this manner, when the light receiving section 5 receives light reflected by each of the fillets 14, each of the fillets 14 formed on both sides of each of the electrode plates 11 are detected as a bright luminescent spot. When a satisfactory fillet 14 is provided to each side of all of the electrode plates 11, as illustrated in FIG. 11A, a high luminance image is acquired for each fillet 14 on each side of all of the electrode plates 11. When a satisfactory fillet 14 is not provided to each side of all of the electrode plates 11, as illustrated in FIG. 11B, a high luminance image cannot be seen at a region where the fillet 14 is absent. Thus, a shape of each of the fillets 14 can be accurately detected.

The apparatus and method for inspecting an electrode plate-connected structure for a secondary cell according to the present invention can evaluate the bonding strength of each of bonded portions based on an image of each of the bonded portions of each electrode plate by irradiating light to an electrode plate-connected structure used as a group of electrode plates for a sealed-type secondary cell, thereby quantitatively and readily evaluating the bonding strength of a plurality of the bonded portions. Moreover, there is no necessity to use expensive, exclusive hardware for image processing, a high-speed CPU, or the like, and thus, the apparatus and method for inspecting an electrode plate-connected structure for a secondary cell according to the present invention are economically advantageous.

Various other modifications will be apparent to and can be readily made by those skilled in the art without departing from the scope and spirit of this invention. Accordingly, it is not intended that the scope of the claims appended hereto be limited to the description as set forth herein, but rather that the claims be broadly construed.

What is claimed is:

1. An inspection apparatus for an electrode plate-connected structure for a secondary cell for inspecting each bonding portion of an electrode plate-connected structure for a secondary cell including a plurality of electrode plates which are arranged in parallel to one another at prescribed intervals and are perpendicularly connected to a power collecting plate, the apparatus characterized by comprising:

a lighting section for irradiating light to each of the bonded portions of the plurality of electrode plates and the power collecting plate of the electrode plate-connected structure for a secondary cell;

a light receiving section for detecting a projected image of each of the bonded portions based on the light irradiated to the electrode plate-connected structure for a secondary cell by the lighting section; and an evaluation section for evaluating a bonding state of each of the bonding portions based on the projected image of each of the bonded portions detected by the light receiving section.

2. An inspection apparatus for an electrode plate-connected structure for a secondary cell according to claim 1, wherein the light receiving section receives light passing through both sides of each of the electrode plates of the electrode plate-connected structure for a secondary cell.

3. An inspection apparatus for an electrode plate-connected structure for a secondary cell according to claim 1, wherein the evaluation section evaluates a bonding state of each of the bonded portions by measuring a height of a lowest point of each of the bonded portions based on the projected image of each of the bonded portions so as to compare the measured height of the lowest point with a reference value.

4. An inspection apparatus for an electrode plate-connected structure for a secondary cell according to claim 1, wherein the evaluation section detects a thickness of each of the plurality of the electrode plates based on the projected image of each of the bonded portions.

5. An inspection apparatus for an electrode plate-connected structure for a secondary cell according to claim 1, wherein the evaluation section detects an inclination state of each of the plurality of the electrode plates based on the projected image of each of the bonded portions.

6. An inspection apparatus for an electrode plate-connected structure for a secondary cell according to claim 1, wherein the evaluation section evaluates a lowest point of each of the bonded portions based on the projected image of each of the bonded portions and a bonding state of each of the bonded portions based on a position of each of the bonded portions which is in contact with a surface of each of the electrode plates located on opposite sides of each of the bonded portions.

7. An inspection apparatus for an electrode plate-connected structure for a secondary cell according to claim 1, wherein the light receiving section receives light reflected by each of the bonded portions.

8. An inspection method for inspecting an electrode plate-connected structure for a secondary cell by inspecting each bonding portion of an electrode plate-connected structure for a secondary cell including a plurality of electrode plates which are arranged in parallel to one another at prescribed intervals and are perpendicularly connected to a power collecting plate, the method characterized by comprising the steps of:

irradiating light to each of the bonded portions of the plurality of electrode plates and the power collecting plate of the electrode plate-connected structure for a secondary cell;

detecting a projected image of each of the bonded portions based on the light irradiated to the electrode plate-connected structure for a secondary cell by the lighting section; and evaluating a bonding state of each of the bonding portions based on the projected image of each of the bonded portions detected by the light receiving section.

9. An inspection method for inspecting an electrode plate-connected structure for a secondary cell according to claim 8, wherein the projected image is acquired based on light passing through both sides of each of the electrode plates of the electrode plate-connected structure for a secondary cell.

10. An inspection method for inspecting an electrode plate-connected structure for a secondary cell according to claim 8, wherein the step of evaluating includes evaluating a bonding state of each of the bonded portions by measuring a height of a lowest point of each of the bonded portions based on the projected image of each of the bonded portions so as to compare the measured height of the lowest point with a reference value.

11. An inspection method for inspecting an electrode plate-connected structure for a secondary cell according to claim 8, wherein the step of evaluating includes detecting a thickness of each of the plurality of the electrode plates based on the projected image of each of the bonded portions.

12. An inspection method for inspecting an electrode plate-connected structure for a secondary cell according to claim 8, wherein the step of evaluating includes detecting an inclination state of each of the plurality of the electrode plates based on the projected image of each of the bonded portions.

13. An inspection method for inspecting an electrode plate-connected structure for a secondary cell according to claim 8, wherein the step of evaluating includes evaluating a lowest point of each of the bonded portions based on the projected image of each of the bonded portions and a bonding state of each of the bonded portions based on a position of each of the bonded portions which is in contact with a surface of each of the electrode plates located on opposite sides of each of the bonded portions.

14. An inspection method for inspecting an electrode plate-connected structure for a secondary cell according to claim 8, wherein the projected image is acquired based on light reflected by each of the bonded portions.

* * * * *